US005780276A

United States Patent [19]

Baniel

[11] Patent Number: 5,780,276
[45] Date of Patent: Jul. 14, 1998

[54] RECOVERY OF CARBOXYLIC ACID FROM ORGANIC SOLUTION THAT CONTAINS AN AMINE AND AN EXTRACTION ENHANCER

[75] Inventor: Avraham Matityahu Baniel, Jerusalem, Israel

[73] Assignee: Innova S.A., Luxembourg, Luxembourg

[21] Appl. No.: 737,792

[22] PCT Filed: May 16, 1995

[86] PCT No.: PCT/EP95/01889

§ 371 Date: Nov. 25, 1996

§ 102(e) Date: Nov. 25, 1996

[87] PCT Pub. No.: WO95/32177

PCT Pub. Date: Nov. 30, 1995

[30] Foreign Application Priority Data

May 23, 1994 [IL] Israel ......................... 109724

[51] Int. Cl.$^6$ ................ C12P 7/40; C07C 51/48; B01D 11/04
[52] U.S. Cl. ................ 435/136; 435/139; 435/141; 435/142; 435/144; 562/580; 562/584; 562/589; 562/593
[58] Field of Search ................ 562/580, 589, 562/584, 593; 435/136, 139, 141, 142, 144

[56] References Cited

U.S. PATENT DOCUMENTS

| 4,275,234 | 6/1981 | Baniel et al. |
| 5,104,492 | 4/1992 | King et al. ............... 562/486 |
| 5,132,456 | 7/1992 | King et al. ............... 562/593 |
| 5,412,126 | 5/1995 | King et al. ............... 562/584 |
| 5,426,219 | 6/1995 | Lehnhardt et al. ............... 562/580 |
| 5,510,526 | 4/1996 | Baniel et al. ............... 562/580 |

FOREIGN PATENT DOCUMENTS

| 0049429 | 4/1982 | European Pat. Off. |
| 0359042 | 3/1990 | European Pat. Off. |

*Primary Examiner*—Herbert J. Lilling
*Attorney, Agent, or Firm*—Browdy and Neimark

[57] ABSTRACT

Recovery of carboxylic acid from an amine-based, water-immiscible organic extractant solution thereof that contains an enhancer, by extraction of the acid into an aqueous phase. A low molecular, at least partly water-miscible organic compound being a $C_2$–$C_5$ alkanol, an acetate of a $C_1$–$C_3$ alkanol and acetone is used as enhancer. In operation, the enhancer is recovered and recycled. The process is applicable, among others, to the recovery of carboxylic acid from a fermentation broth.

20 Claims, 4 Drawing Sheets

RECOVERY OF CARBOXYLIC ACID FROM ORGANIC SOLUTION THAT CONTAINS AN AMINE AND AN EXTRACTION ENHANCER

FIELD OF THE INVENTION

The present invention concerns quite generally the recovery of a carboxylic acid from an amine-based, water-immiscible organic extractant solution thereof obtained by liquid-liquid contact extraction of carboxylic acid from an aqueous starting solution. The term "carboxylic acid" as used herein is to be understood as meaning any aliphatic, cycloaliphatic, aromatic and heterocyclic mono- and polycarboxylic acid and also includes amino acids. The amine-based extractant used for the extraction of the starting solution contains (i) a primary, secondary or tertiary long-chain alkyl amine in which the aggregate number of carbon atoms is at least 20; (ii) a liquid hydrocarbon; and (iii) a polar, non-carboxylic organic compound which during the extraction of the carboxylic acid from the aqueous starting solution serves as extraction enhancer. One typical, but not exclusive field of application of the invention is the recovery of a carboxylic acid from an aqueous fermentation broth, comprising in a first stage a liquid-liquid contact extraction of the fermentation broth with an extractant of the kind specified and in a second stage back-extraction of the carboxylic acid from the organic extractant solution into an aqueous phase.

BACKGROUND OF THE INVENTION

The extraction of carboxylic acid from aqueous solutions by amine-based, water-insoluble organic extractants was described for the first time by Smith and Page, J. Soc. Chem. Ind, 67, 48 (1948). Since then, numerous studies were published and a number of industrial processes established. Typical of the latter is the recovery of citric acid from fermentation broths described in U.S. Pat. No. 4,275,234 (Baniel, et al.), according to which the acid is extracted at low temperature with an amine-containing, water-immiscible organic extractant and subsequently recovered as an aqueous solution by back-extraction with water at a higher temperature. As described in U.S. Pat. No. 4,275,234 and as indeed has become common practice, the extraction power of an amine-containing organic extractant is enhanced by the incorporation of a non-carboxylic, neutral, essentially water insoluble polar organic compound, e.g. an alkanol such as n-octanol, a ketone such as butanone, an ester such as butylacetate, an ether such as dibutylether, a bifunctional compound such as $CH_3.CH_2.CH_2.CH_2OCH2.CH_2OH$ etc. Such compounds, generally referred to as enhancers, modifiers or active diluents, increase the base strength of the amine in the extractant and thereby facilitate the transfer of carboxylic acid from the starting aqueous solution such as a fermentation broth, into the organic extractant phase. Put in other words, the presence of an enhancer shifts the carboxylic acid equilibrium in an aqueous phase/organic extractant phase system in favor of the organic phase. This very shifting of equilibrium, however, creates a problem for the back-extraction in that the transfer of the carboxylic acid from the organic to the aqueous phase is inhibited, and this inhibition may occasionally be so pronounced as to render back-extraction of the organic acid with water impractical even at temperatures close to 100° C.

The fact that in accordance with the prior art only essentially water insoluble enhancers are used is due to the apparent drawbacks that attach to the use of water soluble ones and notably the need to use excess amounts of enhancer and recover it both from the extract and the aqueous extraction residue. Typically, industrial processes use enhancers such as octanol that remain in the organic extractant phase both during extraction and back-extraction by virtue of their water immiscibility.

Several approaches have been proposed to overcome this difficulty, inherent in carboxylic acid recovery processes of this kind. According to one extreme approach, back extraction is foregone altogether and carboxylic acid is recovered from the organic extract by distillation. Obviously, this procedure can be considered only for stable, relatively volatile acids such as acetic acid.

By another approach, back-extraction is carried out above the water boiling temperature so as to increase the degree of hydrolysis of the amine-carboxyl complex and thereby provide for an acceptable rate of back-extraction. This approach requires operation at above atmospheric pressure which is inconvenient and costly in terms of equipment and process control.

By yet another approach the enhancer is removed from the organic phase by distillation prior to back-extraction as described in an extensive study "Extraction of Carboxylic Acids with Amine Extractants", Ind. Eng. Chem. Res. 1990, 29, 1319–1338 in the context of what is described there as "diluent swing". This approach requires that the extractant be so composed that the enhancer boils well below all other constituents and that no decomposition of amine, carboxylic acid or enhancer takes place at the distillation temperature. Even where these requirements can be met, costly, energy-consuming vacuum distillation is as a rule required.

To sum up, the two-stage recovery of carboxylic acid from an aqueous starting solution comprising extraction of the starting solution with an organic amine-based extractant and then back-extraction of the carboxylic acid from the organic extractant into an aqueous phase, poses a technical dilemma with regard to the use of enhancers: while on the one hand the use of an enhancer is highly desirable in the first stage for the purpose of increasing the extraction yield, it impedes the performance of the second stage. There has thus been a long-felt need to solve the problem and provide a method by which carboxylic acid can be effectively recovered from an organic, water-immiscible amine-based extractant solution that also contains an extraction enhancer of the kind specified. It is the object of the present invention to provide such a method.

Enhancers act by virtue of the polar group or groups they contain. Thus, in a series of enhancers of the same polarity, such as normal alkanols for example, the enhancement per unit weight of enhancer increases with the decrease in molecular weight. In spite of this obvious advantage of low molecular weight enhancers they are not used and were never proposed for use. The two most likely reasons for this attach to the fact that low molecular weight enhancers are freely or at least partly water miscible. For one, since the enhancer is part of an extractant that by definition is water immiscible it was natural to avoid the inclusion of a water miscible component. Secondly, enhancer reporting to the aqueous residue of extraction constitutes a loss or impose a cost entailing recovery operation.

BRIEF DESCRIPTION OF THE INVENTION

In accordance with the invention it has surprisingly been found that in a process of the kind specified, a water soluble or partly water-miscible low molecular enhancer can be used; that the excess of such enhancer required during extraction to compensate for losses due to the distribution of enhancer between the two phases, is quite modest; and that as a result such enhancers can be used efficiently. It has further been found that the use of such enhancers in a process of the kind specified minimizes the recovery impeding effect of the enhancer that remains in the extractant solution, and that the enhancer can be recovered from either of the extractant solution and the aqueous phase by conventional means.

Based on this finding the invention provides in a process of recovering a carboxylic acid from an amine-based, water-immiscible organic extractant solution thereof that contains an enhancer, by extraction of the acid into an aqueous phase to yield an aqueous carboxylic acid output solution, the improvement by which the enhancer is a low molecular, at least partly water-miscible organic compound being a member selected from the group of $C_2$–$C_5$ alkanols, acetates of $C_1$–$C_3$ alkanols and acetone, and enhancer is recovered and recycled.

Typical examples of enhancers that can be used in accordance with the invention are ethanol, butanol, acetone and isopropylacetate.

In accordance with one embodiment of the invention, said organic extractant solution is extracted directly with water and enhancer is recovered from the resulting aqueous carboxylic acid output solution. This embodiment is particularly suitable when the enhancer is water soluble at the temperature of operation.

By another embodiment the process comprises extraction of the extractant solution with an aqueous solution of said carboxylic acid to obtain an aqueous acidic enhancer solution and an enhancer-depleted extractant solution, extraction of carboxylic acid from said enhancer-depleted extractant solution into an aqueous phase, and recovery of enhancer from said aqueous acidic enhancer solution. This embodiment is suitable in particular when the invention is practiced with enhancers that at the temperature of operation are only partly water miscible. When practicing this embodiment of the invention, the aqueous carboxylic acid output solution may be combined with the said aqueous acidic enhancer solution to obtain a mixed aqueous solution, from which the enhancer is regained by distillation.

Preferably, the said low molecular, at least partly water miscible enhancer used in accordance with the invention is of a kind that is more volatile than water or that forms with water a low-boiling azeotrope. In this way the enhancer can be regained from an aqueous acidic enhancer solution by distillation without adversely affecting the carboxylic acid.

The invention is applicable to advantage in the production of carboxylic acids by fermentation. By a first embodiment of this application, the invention provides in a process for the recovery of a carboxylic acid from a fermentation broth which comprises extraction of the fermentation broth with an amine-based, water-immiscible organic extractant that includes an enhancer to yield an extractant solution of carboxylic acid and a residual broth, and back-extraction of carboxylic acid from the extractant solution into an aqueous phase to yield an aqueous carboxylic acid output solution and an extractant raffinate, the improvement by which:

(i) the enhancer is a low molecular, at least partly water miscible organic compound being a member selected from the group of $C_2$–$C_5$ alkanols, acetates of $C_1$–$C_3$ alkanols and acetone;

(ii) the said low molecular, at least partly water miscible enhancer is incorporated in the extractant in excess whereby during extraction of the broth an effective amount of enhancer remains in the extractant;

(iii) the back-extraction of carboxylic acid from said extractant solution into an aqueous phase is preceded by extraction of the extractant solution with an aqueous solution of said carboxylic acid to obtain an aqueous acidic enhancer solution and an enhancer depleted extractant solution from which latter, in a subsequent step, carboxylic acid is extracted into an aqueous phase;

(iv) a first amount of enhancer is regained from said acidic aqueous enhancer solution; and (v) a second amount of enhancer is regained from said residual broth.

If desired, the said aqueous acidic enhancer solution may be combined with the said carboxylic acid output solution to obtain a mixed aqueous solution from which the said first amount of enhancer is regained.

By another embodiment of the application of the invention in the production of carboxylic acid by fermentation, there is provided a process for the recovery of carboxylic acid from a fermentation broth which comprises extraction of the fermentation broth with an amine-based, water-immiscible organic extractant that includes an enhancer to yield an extractant solution of carboxylic acid and a residual broth, and back-extraction of carboxylic acid from the extractant solution into an aqueous phase to yield an aqueous carboxylic acid output solution and an extractant raffinate, the improvement by which:

(i) the enhancer is a low molecular organic compound being a member selected from the group of $C_2$–$C_5$ alkanols, acetates of $C_1$–$C_3$ alkanols and acetone and being water soluble at the temperature of operation;

(ii) the said low molecular, water soluble enhancer is incorporated in the extractant in excess whereby during extraction of the fermentation broth an effective amount of enhancer remains in the extractant;

(iii) the said extractant solution of carboxylic acid is back-extracted with water to obtain an aqueous carboxylic acid output solution that contains extractant;

(iv) a first amount of enhancer is regained from said aqueous carboxylic acid output solution; and (v) a second amount of enhancer is regained from said residual broth.

The preferred enhancer in the foregoing embodiment is ethanol.

Preferably, the enhancer in either of these embodiments is of a kind that is more volatile than water or that forms with water a low-boiling azeotrope. In this way enhancer can be regained from the aqueous acidic enhancer solution by distillation without adversely affecting the carboxylic acid.

The excess amount of enhancer required for a given operation in accordance with either of the above two embodiments can be readily established by simple experimentation on the basis of the teachings of the present invention.

Preferably the said extractant raffinate in either of the above two embodiments is recycled for the extraction of enhancer from the said residual broth.

DESCRIPTION OF THE DRAWINGS

For better understanding, the invention will now be described, by way of example only, with reference to the annexed drawing, in which.

DESCRIPTION OF A SPECIFIC EMBODIMENT

Figure 1:
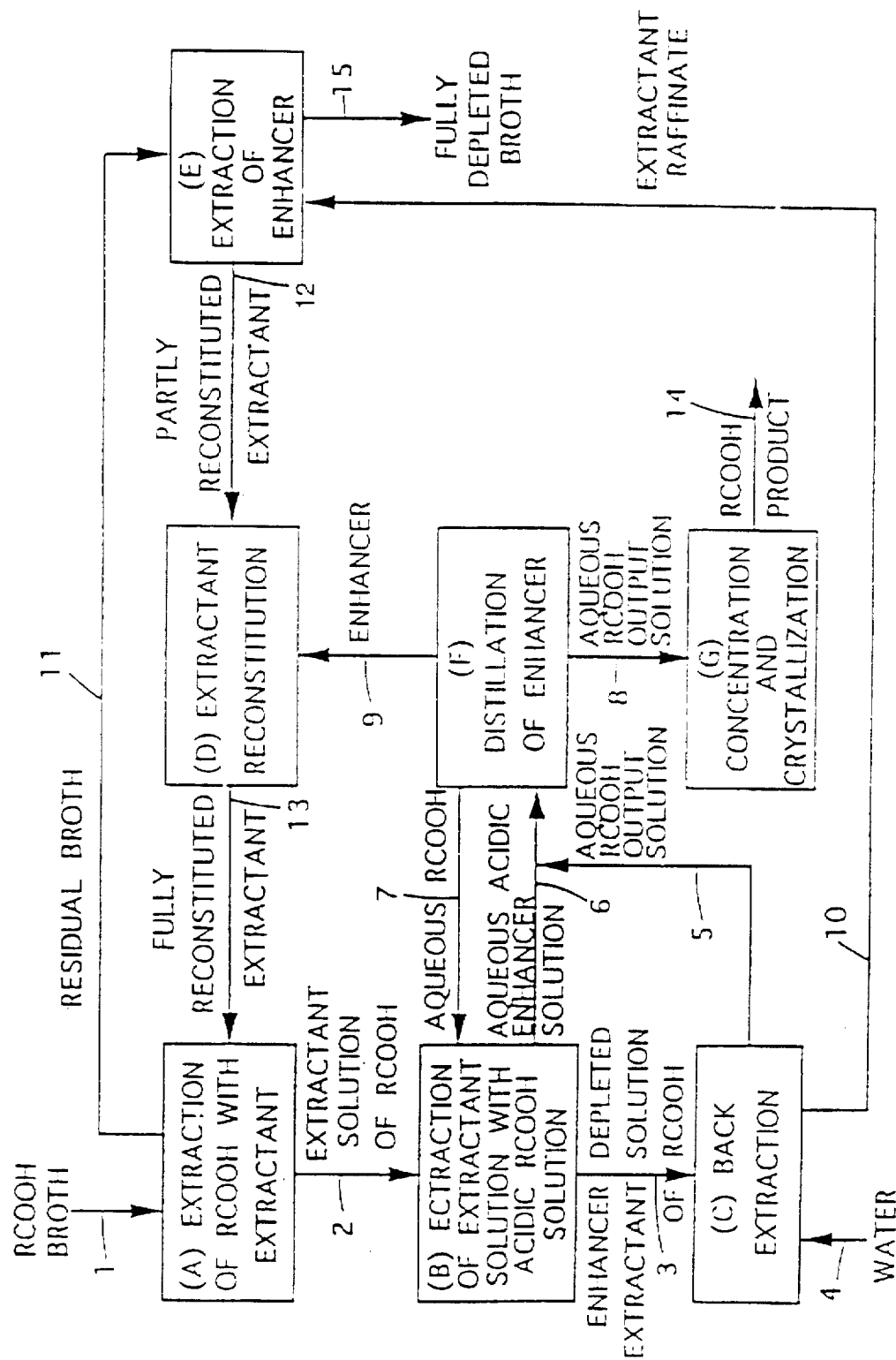
FIGS. 1, 2, 3 and 4 are block diagrams of four embodiments of the process according to the invention.

A typical operation for the recovery of a carboxylic acid, for example citric acid, from a fermentation broth, is illustrated by way of a block diagram in the annexed drawing. As shown, a carboxylic acid fermentation broth is charged at 1 into an extractor A where it is extracted with a fully enhanced, amine-based, water immiscible organic extractant containing an excess of an enhancer of at least partial water miscibility so as to compensate for the enhancer that reports to the aqueous phase. The resulting extractant solution of carboxylic acid is withdrawn at 2 and charged into an extractor B where it is subjected to extraction with an aqueous carboxylic acid solution for the removal of practically all of the enhancer. The remaining, enhancer depleted extractor solution of carboxylic acid is withdrawn at 3 and charged into an extractor C where it is subjected to back-extraction with water introduced at 4. The resulting aqueous carboxylic acid solution is withdrawn at 5 and is combined with an aqueous acidic enhancer solution withdrawn from extractor B at 6 to yield a mixed aqueous solution which is fed into a distillation unit F where enhancer is distilled off. Part of the residual aqueous carboxylic acid solution is returned at 7 into extractor B, and part is withdrawn at 8 as aqueous carboxylic output solution and charged into a crystallizer G.

The condensed enhancer that was distilled off in the distillation unit F is introduced at 9 into a mixer unit D where the extractant is reconstituted.

Extractant raffinate remaining from the back-extraction operation in extractor C is withdrawn at 10 and conducted into an extractor E where it is contacted with residual broth arriving at 11 from the extractor A, whereby extractant that reported to the broth in the course of the extraction operation in extractor A is back-extracted into the extractant. The relative proportions of residual broth and extractant raffinate fed into extractor E are so dosed that essentially all of the extractant reports to the organic phase.

Partly reconstituted extractant is withdrawn from extractor E at 12 and charged into a mixer D together with enhancer arriving from distillation unit F at 9, and the so fully reconstituted extractant is withdrawn at 13 and charged into extractor A.

Product carboxylic acid is withdrawn at 14 and fully depleted broth is withdrawn at 15 as waste.

It should be noted that the distillation of the enhancer in the distillation unit F requires little or even no extra thermal energy beyond that required in any case for concentration and crystallization in crystallizer G.

Since the invention provides for the use of soluble enhancers that are highly effective per unit weight, it allows the use of enhancers in proportions that fully maximize extractant strength. Thus the enhancement of the acidic extraction from the carboxylic acid fermentation broth fed into extractor A is maximized, which is a significant advantage.

It should further be noted that the extraction operation illustrated in the drawing and described hereinbefore with reference thereto, is just one example and that many modifications are conceivable within the framework of the teaching of the present invention.

Figure 2:
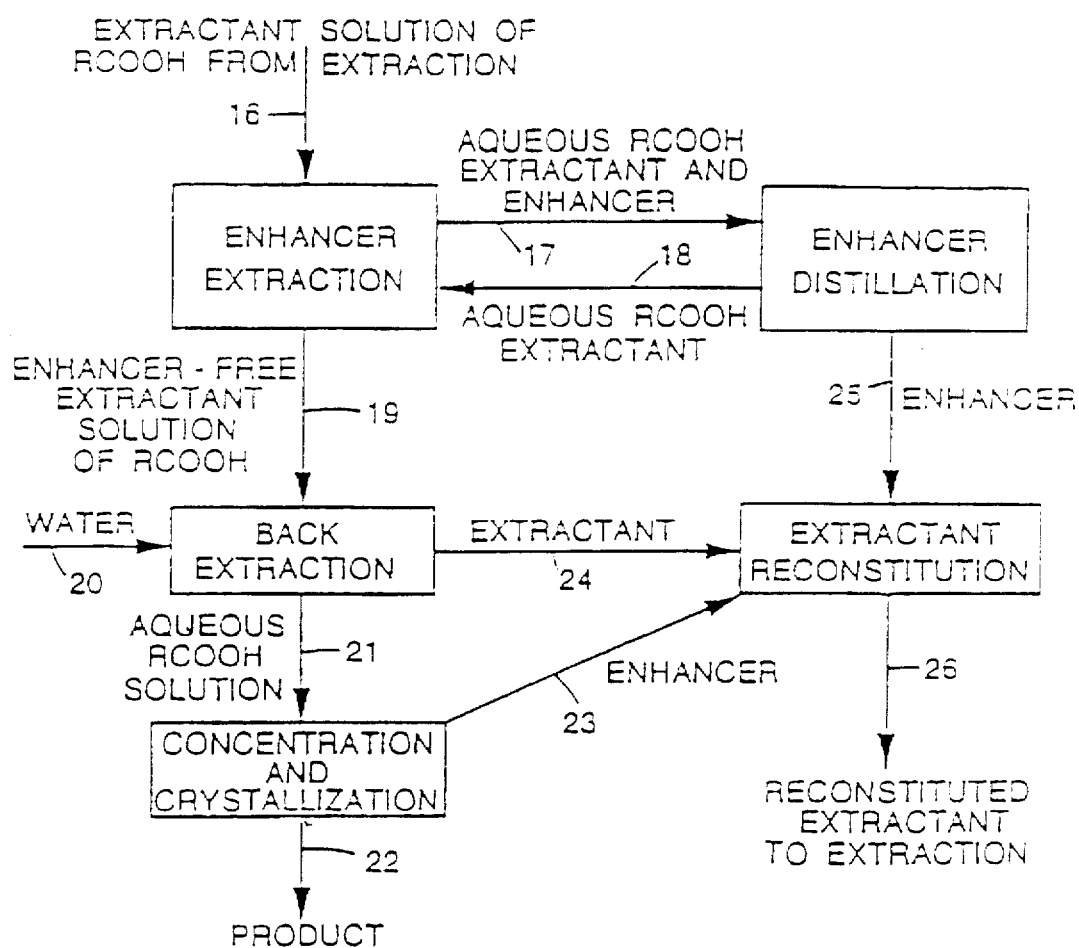

In the embodiment shown in FIG. 2, recovery of carboxylic acid from the fermentation broth with extractant and back-extraction of carboxylic acid with water is assumed to take place at about the same temperature and again practically the entire amount of enhancer is removed from the extractant solution prior to back-extraction. As shown, an extractant carboxylic acid solution resulting from the extraction of a fermentation broth is fed at 16 into an extractor where it is contacted with an aqueous carboxylic acid solution that contains some residual amounts of extractant. The resulting enhancer solution is withdrawn at 17 into an enhancer distillation unit and the remaining enhancer-free extractant solution of carboxylic acid is withdrawn at 19 into an extractor for back-extraction with water arriving at 20. The resulting aqueous carboxylic acid solution is introduced at 21 into a concentrator and crystallizer unit from where the desired product is withdrawn at 22, and distilled off residual enhancer is withdrawn at 23 and conducted into an extractant reconstitution unit together with enhancer arriving at 25 and concurrently with pure extractant withdrawn at 24 from the back-extraction operation. Reconstituted extractant is withdrawn at 26 and recycled to the broth extraction operation.

Figure 3:
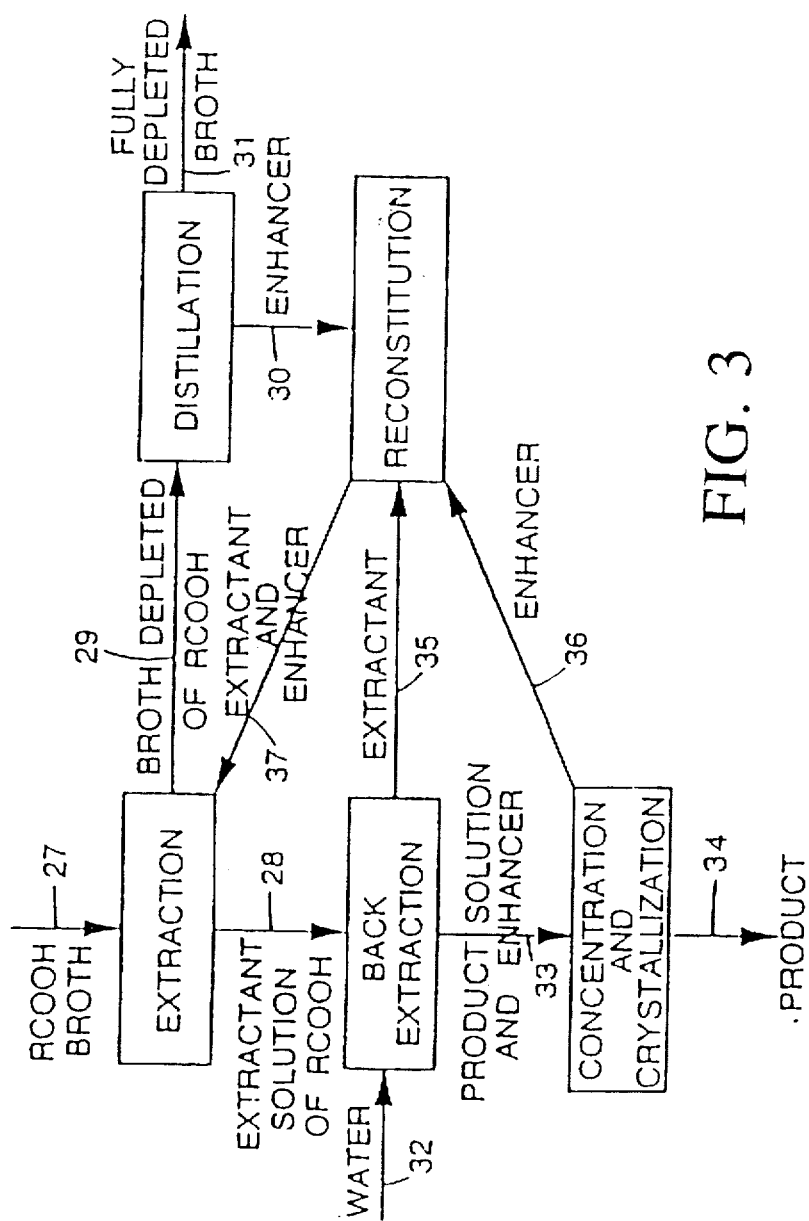

In the embodiment of FIG. 3 back-extraction is assumed to be practiced at a higher temperature than extraction, e.g. in accordance with the teachings in U.S. Pat. No. 4,275,234, and in this case back-extraction is not preceded by separate enhancer extraction. As shown, an RCOOOH broth is fed at 27 into an extractor unit from which an extractant solution of RCOH is withdrawn at 28 and residual broth depleted of carboxylic acid is withdrawn at 29 into a distillation unit from which enhancer is withdrawn at 30 and depleted broth at 31.

The extractant carboxylic acid solution withdrawn at 28 is subjected to back-extraction with water arriving at 32. The resulting aqueous carboxylic acid product solution that contains enhancer is withdrawn at 33 and residual extractant is withdrawn at 34. The carboxylic acid product solution withdrawn at 33 is charged into a concentrator and crystallizer unit from where the product is withdrawn at 34 and distilled off enhancer is withdrawn at 35.

The enhancer withdrawn at 30 and 36 and the extractant withdrawn at 35 are combined in a reconstitution unit and the reconstituted extract/enhancer mixture is recycled to the extraction operation at 37.

Figure 4:
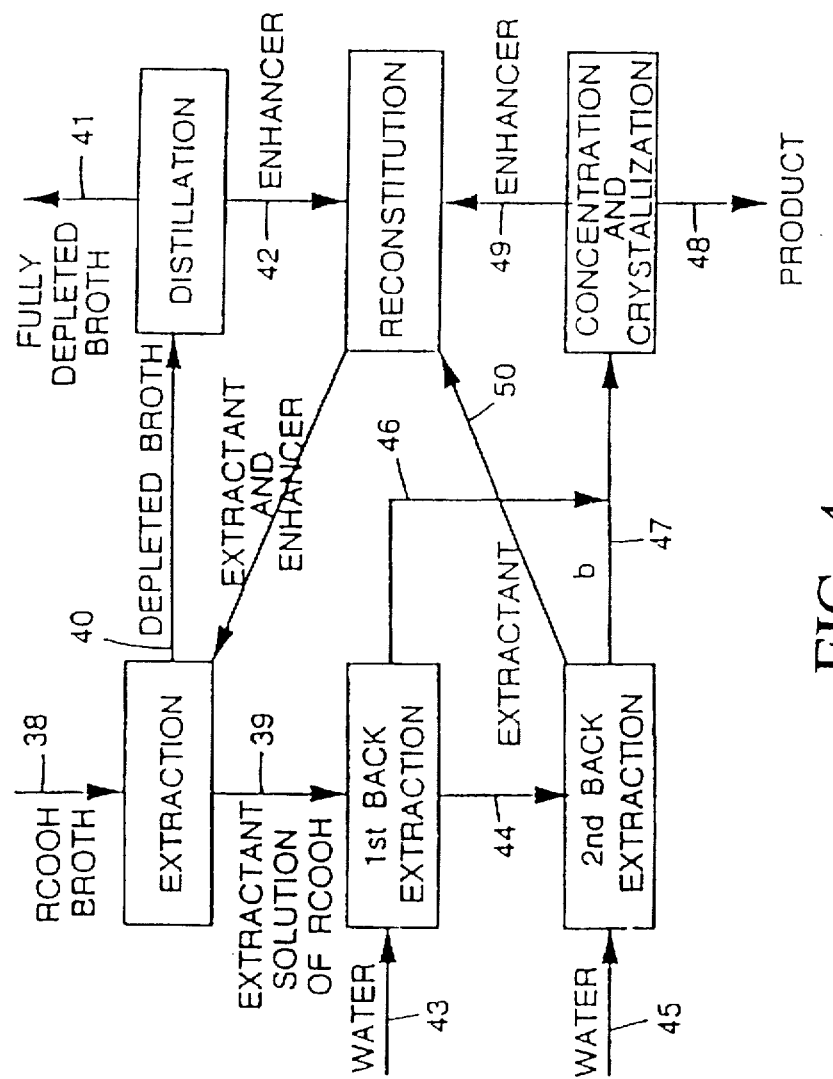

The embodiment of FIG. 4 is essentially similar to that of FIG. 3 but here the water back-extraction is conducted in two stages. As shown, fermentation broth arriving at 38 is charged into an extractor where it is subjected to extraction with an enhancer containing extractant. An extractant solution of carboxylic acid is withdrawn at 39 and a depleted broth at 40. The latter is charged into a distillation unit from where a fully depleted broth is withdrawn at 41 and enhancer is withdrawn at 42. The extractant solution of carboxylic acid withdrawn at 39 is charged into a first extractor for the performance of a first back-extraction stage with water arriving at 43. Partly depleted carboxylic acid extractant solution is withdrawn at 44 into a second extractor for the performance of a second back extraction stage with water arriving at 45. The first aqueous carboxylic acid extract is withdrawn at 46 and the second at 47 and the combined extracts are charged into a concentrator and crystallizer unit from where the product is withdrawn at 48 and additional amounts of distilled enhancer are withdrawn at 49. Depleted extractant is withdrawn from the second back-extraction operation at 50 to a reconstitution unit where it is combined with enhancer arriving at 42 and 49, and the reconstituted extractant/enhancer mixture is recycled to the extraction operation.

The table below, related to citric acid only, illustrates the power and flexibility of the present invention.

| Process | US Pat. No. 4,275,234 | FIG. 2 | FIG. 3 | FIG. 4 |
|---|---|---|---|---|
| Enhancer | octanol | ethanol | ethanol | ethanol |
| % in extractant | 5 | 10 | 10 | 10 |
| citric acid per 1L broth | 190 | 190 | 190 | 190 |
| organic/aqueous volume ratio | 2.1 | 1.1 | 1.1 | 1.1 |
| temperature of Extraction °C. | 20 | 30 | 30 | 30 |
| temperature of back-extraction °C. | 95 | 30 | 95 | 90 |
| Concentration of citric acid in aqueous back-extraction product weight % | 20 | 25 | 27 | 33 |

I claim:

1. In a process of recovering a carboxylic acid from a water-immiscible organic extractant solution thereof which consists essentially of said carboxylic acid, an amine and an extraction enhancer, by extraction of the carboxylic acid into an aqueous phase to yield an aqueous carboxylic acid output solution, the improvement wherein the extraction enhancer is a low molecular, at least partly water miscible organic compound selected from the group consisting of $C_2$–$C_5$ alkanols, acetates of $C_1$–$C_3$ alkanols and acetone, and said extraction enhancer is recovered and recycled.

2. The process of claim 1 wherein said organic extractant solution is extracted directly with water and said extraction enhancer is recovered from the resulting aqueous carboxylic acid output solution.

3. The process of claim 1 comprising (1) extraction of said organic extractant solution with an aqueous solution of said carboxylic acid to obtain an aqueous acidic enhancer solution and an enhancer-depleted organic extractant solution, (2) extraction of carboxylic acid from said enhancer-depleted organic extractant solution into an aqueous phase, and (3) recovery of enhancer from said aqueous acidic enhancer solution.

4. The process of claim 3, wherein said aqueous carboxylic acid output solution is combined with the said aqueous acidic enhancer solution to obtain a mixed aqueous solution from which enhancer is regained by distillation.

5. The process of claim 1, wherein the said low molecular, at least partly water miscible enhancer is of a kind that is more volatile than water or that forms with water a low-boiling azeotrope.

6. In a process for the recovery of a carboxylic acid from a fermentation broth which comprises extraction of said carboxylic acid from the fermentation broth with an amine-based, water-immiscible organic extractant that includes an extraction enhancer to yield an extractant solution of carboxylic acid and a residual broth, and back-extraction of carboxylic acid from the extractant solution into an aqueous phase to yield an aqueous carboxylic acid output solution and an extractant raffinate, the improvement wherein:

(i) the extraction enhancer is a low molecular, at least partly water miscible organic compound selected from the group consisting of $C_2$–$C_5$ alkanols, acetates of $C_1$–$C_3$ alkanols and acetone;

(ii) the said low molecular, at least partly water miscible extraction enhancer is incorporated in the extractant in excess whereby during extraction of the broth an effective amount of extraction enhancer remains in the extractant;

(iii) the back-extraction of carboxylic acid from said extractant solution of carboxylic acid into an aqueous phase is preceded by extraction of the extraction enhancer from the extractant solution with an aqueous solution of said carboxylic acid to obtain an aqueous acidic enhancer solution and an enhancer-depleted organic extractant solution from which latter, in a subsequent step, carboxylic acid is extracted into an aqueous phase;

(iv) a first amount of extraction enhancer is regained from said aqueous acidic enhancer solution; and (v) a second amount of extraction enhancer is regained from said residual broth.

7. The process of claim 6, wherein said aqueous acidic enhancer solution is combined with said carboxylic acid output solution to obtain a mixed aqueous solution from which the said first amount of enhancer is regained.

8. In a process for the recovery of carboxylic acid from a fermentation broth which comprises extraction of said carboxylic acid from the fermentation broth with an amine-based, water-immiscible organic extractant that includes an enhancer to yield an extractant solution of carboxylic acid and a residual broth, and back-extraction of carboxylic acid from the extractant solution into an aqueous phase to yield an aqueous carboxylic acid output solution and an extractant raffinate, the improvement wherein:

(i) the enhancer is a low molecular organic compound selected from the group consisting of $C_2$–$C_5$ alkanols, acetates of $C_1$–$C_3$ alkanols and acetone, and being water soluble at the temperature of operation;

(ii) the low molecular, water soluble enhancer is incorporated in the extractant in excess whereby during extraction of the fermentation broth an effective amount of enhancer remains in the extractant;

(iii) a first amount of enhancer is regained from said aqueous carboxylic acid output solution; and (iv) a second amount of enhancer is regained from said residual broth.

9. The process of claim 6, wherein the low molecular weight enhancer is of a kind that is more volatile than water or that forms with water a low-boiling azeotrope.

10. A process according to claim 6, wherein the said extractant raffinate is recycled for the extraction of enhancer from said residual broth.

11. The process of claim 10, wherein the enhancer is a member selected from the group consisting of ethanol, butanol, acetone and isopropylacetate.

12. The process of claim 8, wherein the low molecular weight enhancer is of a kind that is more volatile than water or that forms with water a low-boiling azeotrope.

13. A process according to claim 8, wherein the said extractant raffinate is recycled for the extraction of enhancer from said residual broth.

14. The process of claim 13, wherein the enhancer is a member selected from the group consisting of ethanol, butanol, acetone and isopropylacetate.

15. The process of claim 2, wherein the said low molecular, at least partly water miscible enhancer is of a kind that is more volatile than water or that forms with water a low-boiling azeotrope.

16. The process of claim 3, wherein the said low molecular, at least partly water miscible enhancer is of a kind that is more volatile than water or that forms with water a low-boiling azeotrope.

17. The process of claim 4, wherein the said low molecular, at least partly water miscible enhancer is of a kind that is more volatile than water or that forms with water a low-boiling azeotrope.

18. A process according to claim 1, wherein said extraction enhancer is selected from the group consisting of ethanol, acetates of C1–C3 alkanols and acetone.

19. A process according to claim 6, wherein said extraction enhancer is selected from the group consisting of ethanol, acetates of C1–C3 alkanols and acetone.

20. A process according to claim 8, wherein said extraction enhancer is selected from the group consisting of ethanol, acetates of $C_1$–$C_3$ alkanols and acetone.

* * * * *